(12) United States Patent
Nose et al.

(10) Patent No.: US 8,791,311 B2
(45) Date of Patent: Jul. 29, 2014

(54) PROCESS FOR PREPARING 1,1,2,3-TETRACHLOROPROPENE

(75) Inventors: Masatoshi Nose, Settsu (JP); Atsushi Suzuki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 13/512,084

(22) PCT Filed: Nov. 24, 2010

(86) PCT No.: PCT/JP2010/071419
§ 371 (c)(1),
(2), (4) Date: May 25, 2012

(87) PCT Pub. No.: WO2011/065574
PCT Pub. Date: Jun. 3, 2011

(65) Prior Publication Data
US 2012/0289751 A1    Nov. 15, 2012

Related U.S. Application Data

(60) Provisional application No. 61/272,975, filed on Nov. 27, 2009.

(51) Int. Cl.
*C07C 17/25*    (2006.01)
(52) U.S. Cl.
CPC ....................................... *C07C 17/25* (2013.01)
USPC .......................................................... 570/226
(58) Field of Classification Search
None
See application file for complete search history.

(56) References Cited

U.S. PATENT DOCUMENTS

| 3,823,195 A | 7/1974 | Smith |
| 4,535,194 A * | 8/1985 | Woodard ...................... 570/236 |
| 2007/0197842 A1 | 8/2007 | Mukhopadhyay et al. |
| 2009/0216055 A1 * | 8/2009 | Wilson et al. ................. 570/219 |

FOREIGN PATENT DOCUMENTS

| EP | 0 131 560 | 1/1985 |
| SU | 213823 | * 3/1968 |
| WO | 2009/085862 | 7/2009 |
| WO | 2010/123148 | 10/2010 |
| WO | 2011/065574 | 6/2011 |

OTHER PUBLICATIONS

English translation of Patent No. SU213823.*
Written Opinion of the International Search Authority issued Apr. 20, 2011 in corresponding International Application No. PCT/JP2010/071419.
R.N. Haszeldine, "676. Fluoro-olefins. Part II. Synthesis and Reactions of Some 3 : 3 : 3-Trihalogenopropenes", Journal of Chemical Society, Letchworth, GB, Jan. 1, 1953, pp. 3371-3378, XP009096268.
International Search Report issued Apr. 20, 2011 in corresponding International Application No. PCT/JP2010/071419.

* cited by examiner

*Primary Examiner* — Fereydoun G Sajjadi
*Assistant Examiner* — Medhanit Bahta
(74) *Attorney, Agent, or Firm* — Wenderoth, Lind & Ponack, L.L.P.

(57) ABSTRACT

The present invention provides a process for preparing 1,1,2,3-tetrachloropropene, including heating 1,1,1,2,3-pentachloropropane in a gas phase in the absence of a catalyst to carry out a dehydrochlorination reaction. According to the process of the present invention, 1,1,2,3-tetrachloropropene (HCC-1230xa) can be efficiently produced by a simple and economically advantageous method that is suitable for industrial-scale production.

12 Claims, 1 Drawing Sheet

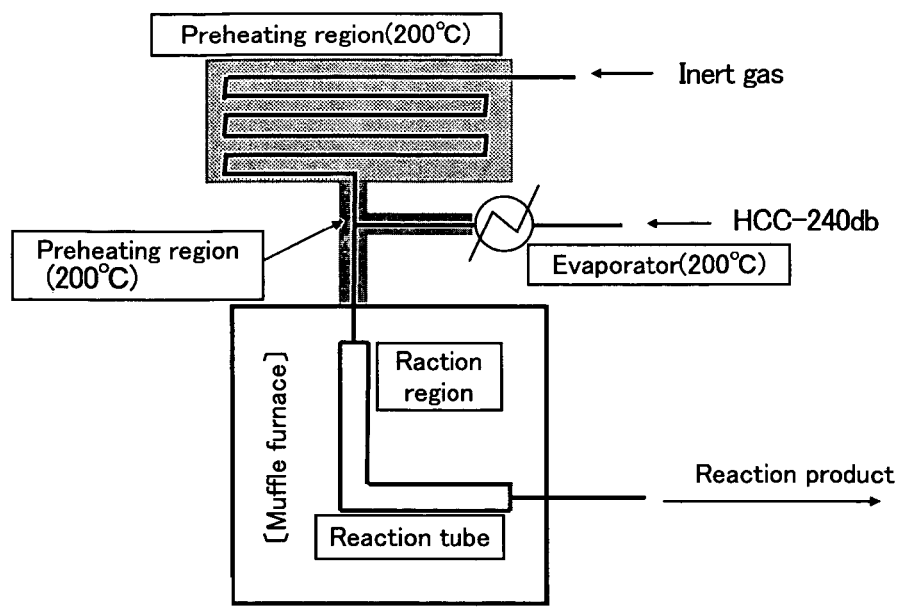

US 8,791,311 B2

PROCESS FOR PREPARING 1,1,2,3-TETRACHLOROPROPENE

This application claims the benefit of U.S. Provisional Application No. 61/272,975, filed Nov. 27, 2009.

TECHNICAL FIELD

The present invention relates to a process for preparing 1,1,2,3-tetrachloropropene.

BACKGROUND ART 1,1,2,3-tetrachloropropene (HCC-1230xa) represented by the formula $CCl_2=CClCH_2Cl$ is a compound that is useful as a material for producing various fluorocarbons, and is also useful as a monomer component for producing various polymers.

As a method for producing HCC-1230xa, for example, Patent Literature 1 listed below discloses a method comprising removing HCl from 1,1,1,2,3-pentachloropropane (HCC-240db, $CCl_3CHClCH_2Cl$) in a liquid phase by using a $FeCl_3$ (ferric chloride) catalyst. Patent Literature 2 listed below also discloses a method comprising removing HCl from HCC-240db in a liquid phase at a temperature of 103° C. or more by using a $FeCl_3$ (ferric chloride) catalyst to directly produce HCC-1230xa from HCC-240db. However, these methods require a long reaction time due to the reaction in a liquid phase; and also have other problems such as high cost due to the use of a catalyst, and waste disposal. Therefore, these methods are not suitable for economical mass production.

Patent Literatures 3 and 4 listed below disclose a method for producing HCC-1230xa comprising subjecting 1,2,3-trichloropropane as a starting compound to a dehydrochlorination reaction with an alkali (NaOH) and a chlorination reaction with chlorine ($Cl_2$), repeating these reactions to form 1,1,2,2,3-pentachloropropane (HCC-240aa), and then removing HCl from 1,1,2,2,3-pentachloropropane. However, this method requires improvement in many respects. For example, the yield is low; a multiple step reaction is required; a large amount of waste generated due to the use of an alkali must be disposed of; and continuous production is difficult because each reaction takes a long time.

Further, Patent Literature 5 listed below discloses that HCC-1230xa can be produced by reacting HCC-240db in a gas phase in the presence of a $ZnCl_2$ catalyst supported on a porous carrier. However, this method requires further improvement in the suppression of side reactions; and also has problems such as high cost due to the use of a catalyst, and catalyst deactivation.

As described above, a process by which HCFC-1230xa can be easily and economically produced at a high yield has yet to be established.

CITATION LIST

Patent Literature

PTL 1: WO 2009/085862 A1
PTL 2: EP 131560 A1
PTL 3: U.S. 2007/0197842 A1
PTL 4: U.S. Pat. No. 3,823,195 A
PTL 5: CAPLUS record number 1968: 451553

SUMMARY OF INVENTION

Technical Problem

The present invention has been made in view of the state of the foregoing prior art. A primary object of the invention is to provide an industrially applicable, simple and economically advantageous process for efficiently preparing 1,1,2,3-tetrachloropropene (HCC-1230xa).

Solution to Problem

The present inventors conducted extensive research to achieve the above object. As a result, the present inventors found the following. A process using 1,1,1,2,3-pentachloropropane (HCC-240db) represented by the formula $CCl_3CHClCH_2Cl$ as a starting compound, and comprising sufficiently heating 1,1,1,2,3-pentachloropropane (HCC-240db) in a gas phase within a specific temperature range in the absence of a catalyst, can produce the target HCC-1230xa at a high yield in a single reaction step, while suppressing side reactions. Thus, this process enables efficient production of HCC-1230xa on an industrial scale, while overcoming the drawbacks of known methods for producing HCC-1230xa. The present invention has been accomplished based on the above findings.

More specifically, the present invention provides the following process for preparing 1,1,2,3-tetrachloropropene (HCC-1230xa).

1. A process for preparing 1,1,2,3-tetrachloropropene comprising heating 1,1,1,2,3-pentachloropropane in a gas phase in the absence of a catalyst to carry out a dehydrochlorination reaction.
2. The process for preparing 1,1,2,3-tetrachloropropene according to Item 1, wherein the heating temperature is 250 to 450° C.
3. The process for preparing 1,1,2,3-tetrachloropropene according to Item 1 or 2, wherein the dehydrochlorination reaction is carried out by simultaneously supplying an inert gas and 1,1,1,2,3-pentachloropropane.
4. The process for preparing 1,1,2,3-tetrachloropropene according to Item 3, wherein the inert gas is supplied in an amount of 0.5 to 100 mol per mol of 1,1,1,2,3-pentachloropropane.
5. A process for preparing 1,1,2,3-tetrachloropropene comprising preparing 1,1,2,3-tetrachloropropene according to the process of any one of Items 1 to 4, and then returning to a reactor unreacted 1,1,1,2,3-pentachloropropane contained in the reaction product, and further 2,3,3,3-tetrachloropropene if 2,3,3,3-tetrachloropropene is contained in the reaction product, to reuse the unreacted 1,1,1,2,3-pentachloropropane and 2,3,3,3-tetrachloropropene.

Hereinafter, the process of the present invention for preparing 1,1,2,3-tetrachloropropene is described in more detail.

(1) Starting Compound

In the present invention, 1,1,1,2,3-pentachloropropane (HCC-240db, bp. 179° C./760 mmHg, 51-53° C./3 mmHg) represented by the formula: $CCl_3CHClCH_2Cl$ is used as a starting compound. By reacting this compound under the conditions described below, the target 1,1,2,3-tetrachloropropene (HCC-1230xa) can be produced in a single reaction step at a high yield. HCC-240db is advantageously used as the starting compound because it is easily available and inexpensive.

(2) Reaction Process

The preparation process of the present invention comprises heating the starting compound in a gas phase to carry out a dehydrochlorination reaction.

In the process of the present invention, it is particularly important to heat the starting compound in the absence of a catalyst to carry out a dehydrochlorination reaction. The reaction carried out by heating the starting compound under such conditions can produce the target 1,1,2,3-tetrachloropropene (HCC-1230xa) in a single reaction step at a high yield, while suppressing side reactions.

In the process of the present invention, the temperature in the reactor is preferably about 200° C. to about 550° C., more preferably about 250° C. to about 450° C., and particularly preferably about 280° C. to about 380° C. Heating within such a temperature range can produce the target 1,1,2,3-tetrachloropropene (HCC-1230xa) with a high selectivity. If the heating temperature is higher than the above-mentioned range, cyclic dimers, dechlorinated 3,3,3-trichloropropene (HCC-1240zf), etc. are produced as by-products, thus resulting in a low selectivity of HCC-1230xa; whereas if the heating temperature is lower, the conversion ratio of the starting compound becomes low. Thus, temperatures out of the above-mentioned range are undesirable.

In the present invention, it is particularly important to sufficiently heat the starting compound within the above temperature range to allow a dehydrochlorination reaction to proceed. Examples of methods preferably used for such heating include: a method of heating the starting compound by using a reaction tube of a sufficient length to prolong the contact time; a method using a reaction tube with a small inner diameter to increase the heat transfer area and thereby improve heat transfer efficiency; and a method of carrying out the reaction using a reaction tube charged with a material that exhibits excellent thermal conductivity, exerts no catalytic activity in the reaction of the present invention, and is stable against the generated hydrogen chloride (HCl), so as to homogenize the temperature distribution within the reaction tube.

The contact time in the reaction, for example, represented by the ratio $V/F_0$ of the gas-phase reaction volume V (cc) relative to the total flow rate $F_0$ (flow rate at 0° C. and 0.1 MPa: cc/sec) of the starting gases passed in the reaction system is preferably in the range of from about 0.1 to about 100 sec, and more preferably from about 1 to about 30 sec, and even more preferably from about 3 to about 25 sec. The "total flow rate of the starting gases" used herein refers to the total flow rate of the 1,1,1,2,3-pentachloropropane used as a starting compound, and the inert gas described below.

In the method using a reaction tube having a small inner diameter to improve the heat transfer efficiency, for example, the relationship of the flow rate of the starting compound to the inner diameter of the reaction tube is preferably adjusted so as to achieve a high linear velocity and a large heat transfer area.

In the method using a reaction tube charged with a material that exerts no catalytic activity, the reaction tube may be charged with Hastelloy pellets, nickel beads, or the like as a material that meets the above-mentioned conditions. The shape of the material charged in the reaction tube is not particularly limited. The material may be of any shape that can be uniformly charged into the reaction tube, such as powders or pellets, and can be selected according to the shape of the reaction tube.

The target 1,1,2,3-tetrachloropropene (HCC-1230xa) can be produced with a particularly high selectivity by heating according to the above-mentioned method in the absence of a catalyst.

According to the process of the present invention, as long as the starting compound is present in a gas state in the above-mentioned reaction temperature region, the starting compound may be supplied in a liquid state. For example, the starting compound in a liquid state may be evaporated using an evaporator (in an evaporation region), and then passed through a preheating region to allow the reaction to proceed in a gas phase. Alternatively, the starting compound may be supplied in a liquid state to a reactor, and then evaporated, when the compound enters a reaction region, to allow the reaction to proceed in a gas phase. The method for evaporating the starting compound in the reaction region is not particularly limited. The starting compound may be evaporated into a gas state, for example, by charging a reaction tube with a material, such as Hastelloy pellets or nickel beads, that exhibits excellent thermal conductivity, exerts no catalytic activity, and is stable to the generated hydrogen chloride (HCl), so as to homogenize the temperature distribution within the reaction tube, heating the reaction tube to a temperature not less than the evaporation temperature of the starting compound, and supplying the starting compound in a liquid state to the reaction tube.

Although the starting compound may be supplied directly to the reactor, supplying the starting compound together with an inert gas to the reaction temperature region is preferable, because such a method particularly suppresses side reactions and produces the target 1,1,2,3-tetrachloropropene (HCC-1230xa) with a high selectivity. Examples of the inert gas include nitrogen, helium, argon, and the like. The inert gas is typically supplied in an amount of about 0.5 to about 100 mol, preferably about 1 to about 30 mol, per mol of the starting compound. By setting the amount of the inert gas within the above-mentioned range, the selectivity of HCC-1230xa can be maintained in a favorable range.

The configuration of the reactor used in the process of the present invention is not particularly limited. For example, an empty column reactor, or a reactor charged with a metal or medium can be used. A material that exhibits excellent thermal conductivity, exerts no catalytic activity in the reaction of the present invention, and is stable against the generated hydrogen chloride (HCl) as mentioned above can be used as the metal or medium to be charged. Various porous or non-porous materials can be used. When such a reactor is used, the inner temperature of the reactor can be raised to a specific temperature range, for example, by externally heating with an electric furnace. Also usable is a multitubular reactor in which a heat-transmitting medium is used to cool the reactor and homogenize the temperature distribution within the reactor. The reactor is preferably formed of a material, such as Inconel, Hastelloy, Monel, or Incoloy, that is resistant to the corrosive action of hydrogen chloride.

There is no limitation on the pressure during the reaction insofar as the starting compound is present in a gas state. Any pressure such as normal pressure, increased pressure, or reduced pressure can be used. More specifically, the preparation process of the present invention may be carried out under reduced pressure or at atmospheric pressure (0.1 MPa), or may be carried out under increased pressure insofar as the starting compound does not turn into a liquid state.

When the reaction is carried out under the above-mentioned conditions, a reaction product containing 1,1,2,3-tetrachloropropene (HCC-1230xa) can be obtained at the reactor outlet. HCC-1230xa can be purified and collected by distillation etc. The obtained HCC-1230xa may be used directly for a desired purpose, or may be converted into another compound.

The reaction product obtained by the preparation process of the present invention may contain, in addition to HCC-1230xa, an isomer 2,3,3,3-tetrachloropropene (HCC-1230xf) represented by the formula $CCl_3CCl=CH_2$. This compound is produced as a precursor of HCC-1230xa, depending on the reaction conditions, and can be converted to the target HCC-1230xa by heating under the same conditions as in the present invention.

According to the preparation process of the present invention, after HCC-1230xa is isolated and collected from the reaction product, the unreacted starting compound (HCC-240db) contained in the reaction product may be returned to the reactor and reused as a starting compound. When the reaction product contains HCC-1230xf, HCC-1230xf can also be returned to the reactor and reused.

The process of the present invention can produce the target 1,1,2,3-tetrachloropropene (HCC-1230xa) with a high selectivity. Therefore, even if the conversion ratio of the starting compound is low, a high productivity can be maintained by recycling the precursor of HCC-1230xa and unreacted starting compound.

Advantageous Effects of Invention

According to the process of the present invention, 1,1,2,3-tetrachloropropene (HCC-1230xa) can be prepared with a high selectivity in a single step reaction by using 1,1,1,2,3-pentachloropropane (HCC-240db) as a starting compound.

Further, the process of the present invention can be performed under mild conditions such as normal pressure or reduced pressure, and the process utilizes a gas phase reaction that is suitable for continuous production.

Furthermore, the process of the present invention overcomes all of the drawbacks of known preparation processes using catalysts, and can produce the target 1,1,2,3-tetrachloropropene with a higher selectivity.

Therefore, the process of the present invention is an industrially highly advantageous method for producing 1,1,2,3-tetrachloropropene (HCC-1230xa).

BRIEF DESCRIPTION OF DRAWINGS

FIG. 1 is a schematic diagram of the reactor used in Examples 1 to 4.

DESCRIPTION OF EMBODIMENTS

The present invention is described below in more detail with reference to Production Examples of 1,1,1,2,3-pentachloropropane (HCC-240db), which is used as a starting compound, and with reference to Examples of the present invention.

Production Example 1

1,1,1,2,3-Pentachloropropane (HCC-240db) was prepared by sequentially performing the following Steps (1) to (3).

(1) Preparation of 1,1,1,3-tetrachloropropane (HCC-250fb)

A 1,000 ml autoclave equipped with a thermometer, a vacuum line, a nitrogen purge line, a feeding line, a gauge, and a pressure relief valve was charged with 9.72 g (171 mmol) of soft iron powder, 48 g (260 mmol) of triethyl phosphate, 200 mg of ferric chloride, and 810 g (5.26 mol) of carbon tetrachloride; and then purged 5 times with nitrogen, and once with ethylene. The autoclave was evacuated and charged, under stirring, with ethylene to a gauge pressure of 0.4 MPa. When the autoclave was heated to 110° C., the reaction was initiated. The internal temperature was increased to 134° C., while the pressure was decreased from 0.8 MPa to 0.25 MPa. While the ethylene pressure was maintained at 0.8 MPa, stirring was performed at an internal temperature of 120° C. for 9 hours. Thereafter, 24 g (130 mmol) of triethyl phosphate was forced into the autoclave, and the reaction was allowed to proceed at 120° C. for 7 hours.

After completion of the reaction, the crude product was analyzed by gas chromatography, and complete consumption of carbon tetrachloride was thereby confirmed. The crude product was washed twice with water having a volume 3 times that of the crude product, and the organic layer was dried over magnesium sulfate to obtain HCC-250fb having a purity of 79.8%, as determined by gas chromatography. An oligomer in which HCl was added to ethylene was obtained as a by-product.

The obtained crude product was distilled under reduced pressure (10 mmHg), and a fraction at 70° C. to 74° C. was collected to obtain 814 g (4.94 mol, yield: 91%) of HCC-250fb at a purity of 98% or more.

(2) Preparation of 1,1,3-trichloropropene (HCC-1240za) and 3,3,3-trichloropropene (HCC-1240zf)

A 1,000 ml four-necked flask equipped with a thermometer and a condenser tube was charged with 540 g (3.0 mol) of HCC-250fb obtained in Step (1), 630 g of a 40% aqueous KOH solution, and 10 g of a phase-transfer catalyst (Aliquat 336). The reaction was allowed to proceed under stirring at 80° C. in an oil bath for 3 hours. After completion of the reaction, the resulting product was cooled and distilled under reduced pressure (10 to 20 mmHg), and a fraction at 67.7° C. to 81.9° C. was collected to obtain 390 g (2.68 mol, yield: 89.3%) of a mixture of HCC-1240zf and HCC-1240za with a HCC-1240zf: HCC-1240za ratio of 62:38.

(3) Preparation of 1,1,1,2,3-pentachloropropane (HCC-240db)

A 500 ml flask equipped with a high-pressure mercury vapor lamp, a magnetic stirrer, and two gas ports was charged with 265 g of a mixture of the 1,1,3-trichloropropene (HCC-1240za) and 3,3,3-trichloropropene (HCC-1240zf) obtained in Step (2), and allowed to cool to 0° C. in an ice bath. While the content was irradiated with ultraviolet light, stirring was performed, and chlorine gas was introduced at 20 to 120 mL/min from one of the gas ports to the area above the liquid surface of the content. The reaction mixture was intermittently sampled, and analyzed by gas chromatography to measure the degree of chlorination. After 3 hours, the trichloropropene was entirely consumed, and 370 g of a product was obtained. The obtained product was distilled under reduced pressure (3 mmHg), and a fraction at 51° C. to 53° C. was collected to obtain 330 g of 1,1,1,2,3-pentachloropropane (HCC-240db) at a purity of 99.6%.

Example 1

FIG. 1 is a schematic diagram of the reactor used in the Example. For this reactor, a tubular reaction vessel (a reaction tube, internal volume: 24.4 cm$^3$) made of Inconel 600, having an outer diameter of ¼ inches (thickness: 1.0 mm), and a length of 164.0 cm was placed into a muffle furnace, and a line for supplying HCC-240db and inert gas was connected to the inlet-side connection of the reaction tube. The HCC-240db supply line was equipped with an evaporator to allow HCC-240db supplied in a liquid state to be evaporated at 200° C. The evaporated HCC-240db was preheated at 200° C. until it was supplied to the reactor. In the case of supplying an inert gas, the inert gas supply line was also preheated at 200° C., and the inert gas was supplied to the reactor as a mixture with HCC-240db. The inlet- and outlet-side connections of the reaction tube were connected to pipes having an outer diameter of ⅛ inches, and the inner space of the pipes in the muffle furnace was also regarded as a reaction space. The reaction space volume in the muffle furnace including the pipes was 25.2 cm$^3$. All of the pipes and joints other than the reaction tube were made of Hastelloy.

The inner space temperature of the muffle furnace was measured at two points, and the average temperature thereof was determined as the furnace temperature. The outer wall temperature of the reaction tube was measured at six points at equal intervals from the inlet side to the outlet side of the reaction tube, and the average temperature thereof was determined as the reaction temperature. While the pressure in the reaction tube was set to atmospheric pressure (0.1 MPa) and the reaction temperature was maintained at 400° C., nitrogen ($N_2$) was continuously introduced into the reaction tube at 200 cc/min (flow rate at 0° C. and 0.1 MPa) for 15 hours.

Thereafter, the reaction temperature was lowered to 350° C., and the flow rate of nitrogen ($N_2$) was changed to 140 cc/min (at 0° C. and 0.1 MPa). While supplying nitrogen at 140 cc/min, 1,1,1,2,3-pentachloropropane (HCC-240db, 99.6% of purity) was continuously supplied at 7.0 cc/min (flow rate at 0° C. and 0.1 MPa) to initiate the reaction. The furnace temperature was adjusted so as to maintain the reaction temperature at 350° C. The molar ratio of nitrogen ($N_2$) to 1,1,1,2,3-pentachloropropane ($N_2$/1,1,1,2,3-pentachloropropane) was 20. The contact time ($V/F_0$) calculated from the reaction space volume (V) in the muffle furnace and the total flow rate ($F_0$) of the reactant was 10.2 sec.

The outflow from the reactor obtained 3 hours after the initiation of the reaction was analyzed by gas chromatography. The reaction product was quantified in the following manner. A predetermined amount of perchloroethylene was dissolved as an internal standard substance in HCFC-225 (225ca:225cb=57:43), and the resulting solution was mixed with ice water for liquid separation. The outflow of the reactor was bubbled into the HCFC-225 layer for a predetermined period of time, so that an organic substance was extracted with the HCFC-225 layer, and hydrogen chloride was dissolved in the ice water.

The extract was heated to 20° C., and the HCFC-225 layer was analyzed by gas chromatography (FID) using a DB-1 (60 m) capillary column as the column. The conversion ratio of the starting compound and the selectivity of each of the products were calculated by converting the amount of each product to a molar ratio, based on the ratio of the detected area of each product to that of perchloroethylene used as the internal standard substance, while considering coefficients in gas chromatography. Table 1 shows the results of quantification of the components obtained from the reactor outlet according to the above method.

The reaction product obtained in this Example contained the following components:
$CCl_2$=$CClCH_2Cl$ (HCC-1230xa)
$CCl_3CCl$=$CH_2$ (HCC-1230xf)
$CCl_3CH$=$CH_2$ (HCC-1240zf)

Example 2

The reaction was performed under the same conditions as in Example 1, except that the reaction tube was changed to a tubular reactor made of Inconel 600 with an outer diameter of ½ inches (thickness: 1.24 mm) and a length of 2.0 m (a reaction tube, internal volume: 164.0 cm$^3$); the amount of nitrogen ($N_2$) supplied was changed to 200 cc/min (flow rate at 0° C. and 0.1 MPa); the amount of 1,1,1,2,3-pentachloropropane (HCC-240db, purity: 99.6%) supplied was changed to 10.0 cc/min (flow rate at 0° C. and 0.1 MPa); and the reaction temperature was changed to 400° C. The molar ratio of nitrogen ($N^2$) to 1,1,1,2,3-pentachloropropane ($N_2$/1,1,1,2,3-pentachloropropane) was 20. The contact time ($V/F_0$) calculated from the reaction space volume (V) in the muffle furnace and the total flow rate ($F_0$) of the reactant was 47.0 sec. Table 1 shows the analysis results obtained three hours after the initiation of the reaction.

Example 3

The reaction was performed under the same conditions as in Example 1, except that the reaction tube was changed to a tubular reactor made of Inconel 600 with an outer diameter of ¼ inches (thickness: 1.0 mm) and a length of 2.75 m (a reaction tube, internal volume: 39.5 cm$^3$); the amount of nitrogen ($N_2$) supplied was changed to 100 cc/min (flow rate at 0° C. and 0.1 MPa); the amount of 1,1,1,2,3-pentachloropropane (HCC-240db, purity: 99.6%) supplied was changed to 10.0 cc/min (flow rate at 0° C. and 0.1 MPa); and the reaction temperature was changed to 285° C. The molar ratio of nitrogen ($N_2$) to 1,1,1,2,3-pentachloropropane ($N_2$/1,1,1,2,3-pentachloropropane) was 10. The contact time ($V/F_0$) calculated from the reaction space volume (V) in the muffle furnace and the total flow rate ($F_0$) of the reactant was 22.0 sec. Table 1 shows the analysis results obtained two hours after the initiation of the reaction.

Example 4

The reaction was performed under the same conditions as in Example 1, except that the reaction tube was changed to a tubular reactor made of Inconel 600 with an outer diameter of ⅛ inches (thickness: 0.7 mm) and a length of 3.05 m (a reaction tube, internal volume: 7.53 cm$^3$); the supply of nitrogen ($N_2$) was stopped; and the amount of 1,1,1,2,3-pentachloropropane (HCC-240db, purity: 99.6%) supplied was changed to 20.0 cc/min (flow rate at 0° C. and 0.1 MPa). The molar ratio of nitrogen ($N_2$) to 1,1,1,2,3-pentachloropropane ($N_2$/1,1,1,2,3-pentachloropropane) was 0. The contact time ($V/F_0$) calculated from the reaction space volume (V) in the muffle furnace and the total flow rate ($F_0$) of the reactant was 24.9 sec. Table 1 shows the analysis results obtained three hours after the initiation of the reaction.

TABLE 1

|  | Example 1 | Example 2 | Example 3 | Example 4 |
|---|---|---|---|---|
| Reaction temperature (° C.) | 350 | 400 | 285 | 350 |
| V/F$_0$ (sec) | 10.2 | 47.0 | 22.0 | 24.9 |
| Conversion ratio of HCC-240db (%) | 75.4 | 73.4 | 48.8 | 77.6 |
| Selectivity of the product (%) |  |  |  |  |
| HCC-1230xa | 97.9 | 90.3 | 96.8 | 88.3 |
| HCC-1230xf | 1.6 | 1.5 | 2.3 | 2.0 |
| HCC-1240zf | 0.4 | 5.4 | 0.6 | 4.9 |
| Others | 0.1 | 2.8 | 0.3 | 4.8 |

The invention claimed is:
1. A process for preparing 1,1,2,3-tetrachloropropene, comprising heating 1,1,1,2,3-pentachloropropane in a gas phase in the absence of a catalyst to carry out a dehydrochlorination reaction.

2. The process for preparing 1,1,2,3-tetrachloropropene according to claim 1, wherein the heating temperature is 250 to 450° C.

3. The process for preparing 1,1,2,3-tetrachloropropene according to claim 1, wherein the dehydrochlorination reaction is carried out by simultaneously supplying an inert gas and 1,1,1,2,3-pentachloropropane.

4. The process for preparing 1,1,2,3-tetrachloropropene according to claim 3, wherein the inert gas is supplied in an amount of 0.5 to 100 mol per mol of 1,1,1,2,3-pentachloropropane.

5. A process for preparing 1,1,2,3-tetrachloropropene, comprising
obtaining 1,1,2,3-tetrachloropropene and optionally 2,3,3,3-tetrachloropropene by heating 1,1,1,2,3-pentachloropropane in a gas phase in the absence of a catalyst to carry out a dehydrochlorination reaction in a reactor, and
recycling unreacted 1,1,1,2,3-pentachloropropane and the optional 2,3,3,3-tetrachloropropene by returning the unreacted 1,1,1,2,3-pentachloropropane and the optional 2,3,3,3-tetrachloropropene to the reactor.

6. The process for preparing 1,1,2,3-tetrachloropropene according to claim 2, wherein the dehydrochlorination reaction is carried out by simultaneously supplying an inert gas and 1,1,1,2,3-pentachloropropane.

7. The process for preparing 1,1,2,3-tetrachloropropene according to claim 6, wherein the inert gas is supplied in an amount of 0.5 to 100 mol per mol of 1,1,1,2,3-pentachloropropane.

8. The process for preparing 1,1,2,3-tetrachloropropene according to claim 5, wherein the heating temperature is 250 to 450° C.

9. The process for preparing 1,1,2,3-tetrachloropropene according to claim 5, wherein the dehydrochlorination reaction is carried out by simultaneously supplying an inert gas and 1,1,1,2,3-pantachloropropane.

10. The process for preparing 1,1,2,3-tetrachloropropene according to claim 9, wherein the inert gas is supplied in an amount of 0.5 to 100 mol per mol of 1,1,1,2,3-pentachloropropane.

11. The process for preparing 1,1,2,3-tetrachloropropene according to claim 8, wherein the dehydrochlorination reaction is carried out by simultaneously supplying an inert gas and 1,1,1,2,3-pantachloropropane.

12. The process for preparing 1,1,2,3-tetrachloropropene according to claim 11, wherein the inert gas is supplied in an amount of 0.5 to 100 mol per mol of 1,1,1,2,3-pentachloropropane.

* * * * *